United States Patent [19]

Watts

[11] Patent Number: 4,459,300
[45] Date of Patent: Jul. 10, 1984

[54] PHARMACEUTICALLY ACTIVE AZA-BICYCLO BENZAMIDE DERIVATIVES

[75] Inventor: Eric A. Watts, Harlow, England
[73] Assignee: Beecham Group p.l.c., England
[21] Appl. No.: 389,436
[22] Filed: Jun. 17, 1982

[30] Foreign Application Priority Data

Jun. 29, 1981 [GB] United Kingdom ............... 8119998

[51] Int. Cl.³ ................... A61K 31/46; C07D 451/04
[52] U.S. Cl. ................................. 424/265; 424/274;
424/278; 424/263; 424/275; 424/244; 260/239
BF; 260/244.4; 260/245.7; 546/124; 546/125;
546/126; 546/112; 548/452
[58] Field of Search ................... 546/124, 125, 126;
548/452; 424/265; 260/244.4, 245.7, 239 BF

[56] References Cited

U.S. PATENT DOCUMENTS 4,273,778 6/1981 Hadley et al. ................... 424/265

FOREIGN PATENT DOCUMENTS

| | | |
|---|---|---|
| 13138 | 7/1980 | European Pat. Off. . |
| 31219 | 7/1981 | European Pat. Off. . |
| 2446823 | 8/1980 | France . |
| 2476088 | 8/1981 | France . |
| 2042522 | 9/1980 | United Kingdom . |

OTHER PUBLICATIONS

EPX European Pat. Off. 0055524-7/82.

Primary Examiner—John M. Ford
Assistant Examiner—Bernard Dentz
Attorney, Agent, or Firm—Jacobs & Jacobs

[57] ABSTRACT

Compounds of formula (I) and pharmaceutically acceptable salts thereof:

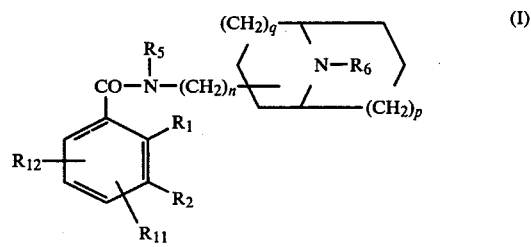

wherein:
n, p and q independently are 0 to 2;
$R_5$ is hydrogen or $C_{1-6}$ alkyl;
$R_6$ is $C_{1-7}$ alkyl or a group —$(CH_2)_sR_7$ where s is 0 to 2 and $R_7$ is a $C_{3-8}$ cycloalkyl group, or a group —$(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen, or a thienyl group;
$R_{12}$ is $C_{1-6}$ alkylsulphonyl;
and either
$R_1$ is $C_{1-6}$ alkoxy or $C_{1-6}$ alkylthio; and one of $R_2$ and $R_{11}$ is hydrogen and the other is $C_{1-6}$ alkoxy, $C_{1-6}$ alkyl or hydroxy; or $R_1$ and $R_2$ together are $C_{1-3}$ alkylenedioxy; and $R_{11}$ is hydrogen, halogen, $CF_3$, $C_{1-6}$ alkoxy, hydroxy, nitro, $C_{1-7}$ acyl, amino, $C_{1-7}$ acylamino, aminocarbonyl optionally substituted by one or two $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by one or more halogen, trifluoromethyl, $C_{1-6}$ alkoxy or nitro groups or N-disubstituted by $C_{4-6}$ polymethylene, having useful pharmacological activity, e.g. in the treatment of impaired gastric motility, a process for their preparation and their use.

19 Claims, No Drawings

PHARMACEUTICALLY ACTIVE AZA-BICYCLO BENZAMIDE DERIVATIVES

This invention relates to novel compounds, to pharmaceutical compositions containing them, and to a process for their preparation.

European Patent Application No. 79302978.6 and U.S. Pat. No. 4,273,778 disclose that compounds of the formula (A), and pharmaceutically acceptable salts thereof:

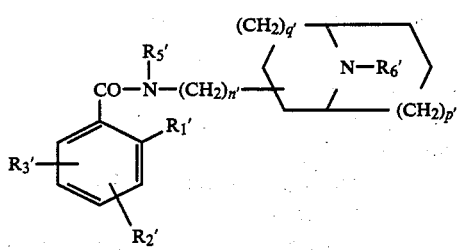

wherein:

$R_1'$ is a $C_{1-6}$ alkoxy group;

$R_2'$ and $R_3'$ are the same or different and are hydrogen, halogen, $CF_3$, $C_{2-7}$ acyl, $C_{2-7}$ acylamino, or amino, aminocarbonyl or aminosulphone optionally substituted by one or two $C_{1-6}$ alkyl groups, $C_{1-6}$ alkylsulphone or nitro;

$R_5'$ is hydrogen or $C_{1-6}$ alkyl;

$R_6'$ is $C_{1-7}$ alkyl or a group $—(CH_2)_sR_7'$ where s' is 0 to 2 and $R_7'$ is a $C_{3-8}$ cycloalkyl group, or a group $—(CH_2)_tR_8'$ where t is 1 or 2 and $R_8'$ is $C_{2-5}$ alkenyl or a phenyl group optionally substituted by one or two substituents selected from $C_{1-6}$ alkyl, $C_{1-4}$ alkoxy, trifluoromethyl and halogen; and n', p' and q' are independently 0 to 2; have useful pharmacological activity. More specifically the compounds of formula (A) are stated to be useful in the treatment of disorders related to impaired gastro-intestinal motility and/or in the treatment of disorders of the central nervous system. All the compounds are stated to have anti-emetic activity.

The said European and U.S. Patent Applications, the subject matter of which is imported herein by reference, has extensive exemplification of typical compounds of the formula (A) and of their pharmacological activity, establishing the veracity of the claimed utilities for the class of compounds defined by formula (A).

In the said formula (A) $R_3'$ may be a $C_{1-6}$ alkylsulphonyl group (R—SO$_2$—). It has now been discovered that certain $C_{1-6}$ alkylsulphonyl compounds of a structure distinct from that of formula (A), also have useful pharmacological activity.

Accordingly the present invention provides a compound of the formula (I), and pharmaceutically acceptable salts thereof:

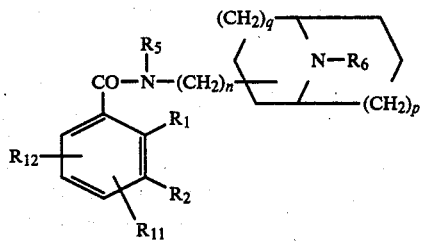

wherein:

n, p and q independently are 0 to 2;

$R_5$ is hydrogen or $C_{1-6}$ alkyl;

$R_6$ is $C_{1-7}$ alkyl or a group $—(CH_2)_sR_7$ where s is 0 to 2 and $R_7$ is a $C_{3-8}$ cycloalkyl group, or a group $—(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen, or a thienyl group;

$R_{12}$ is $C_{1-6}$ alkylsulphonyl;

and either $R_1$ is $C_{1-6}$ alkoxy or $C_{1-6}$ alkylthio; and one of $R_2$ and $R_{11}$ is hydrogen and the other is $C_{1-6}$ alkoxy, $C_{1-6}$ alkyl or hydroxy; or $R_1$ and $R_2$ together are $C_{1-3}$ alkylenedioxy; and $R_{11}$ is hydrogen, halogen, $CF_3$, $C_{1-6}$ alkoxy, hydroxy, nitro, $C_{1-7}$ acyl, amino, $C_{1-7}$ acylamino, aminocarbonyl optionally substituted by one or two $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups any of which phenyl moieties may be substituted by one or more halogen, trifluoromethyl, $C_{1-6}$ alkoxy or nitro groups or N-disubstituted by $C_{4-6}$ polymethylene.

Suitable examples of $R_5$ include hydrogen, methyl, ethyl, n- and iso-propyl, n-, sec- and tert-butyl, preferably hydrogen or methyl, in particular hydrogen.

Suitable examples of $R_6$ when $C_{1-7}$ alkyl include methyl, ethyl, n- and iso-propyl and n-, sec-, iso- and tert-butyl, n-pentyl, n-hexyl, n-heptyl and 3-methylbutyl 4-methylpentyl and 5-methylpentyl. Within $C_{1-7}$ alkyl radicals, $C_{1-4}$ alkyl are particularly useful.

Suitable examples of $R_6$ when $C_{1-4}$ alkyl include methyl, ethyl, n- and iso-propyl and n-, sec-, iso- and tert-butyl, particularly methyl, n-propyl and sec-butyl.

Similarly, within $C_{1-7}$ alkyl radicals, $C_{5-7}$ alkyl are also of interest.

Suitable examples of $R_6$ when $C_{5-7}$ alkyl include n-pentyl, n-hexyl and n-heptyl, 3-methylbutyl, 4-methylpentyl and 5-methylhexyl.

When $R_6$ is a group $—(CH_2)_sR_7$ as defined, suitable examples of $R_7$ include $C_{5-8}$ cycloalkyl, preferably cyclohexyl. s is preferably 1.

When $R_6$ is a group $—(CH_2)_tR_8$ as defined, t is preferably 1.

In such a group $R_6$, when $R_8$ is $C_{2-5}$ alkenyl, suitable examples thereof include vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl, in their E and Z forms where stererisomerism exists.

A preferred $C_{1-5}$ alkenyl $R_8$ radical is vinyl, so that $R_6$ is preferably allyl.

When $R_8$ is optionally substituted phenyl as defined above, suitable examples of such optional phenyl substitutents include methyl, ethyl, n- and iso-propyl, n-, sec- and tert-butyl; methoxy, ethoxy, n- and iso-propoxy; $CF_3$, fluoro, chloro or bromo. Preferably $R_8$ when optionally substituted phenyl is unsubstituted. When $R_8$ is thienyl it may be 2- or 3-thienyl, generally 2-thienyl.

Two values for $R_6$ are optionally substituted benzyl as hereinbefore defined and thienylmethyl (also called thenyl). Optionally substituted benzyl is favoured, preferably benzyl.

Compounds of the formula (I) wherein $R_6$ is $-(CH_2)_sR_7$ and $-(CH_2)_tR_8$ as defined, and wherein $R_6$ contains at least 5 carbon atoms, are of particular interest because of their beneficial pharmacological activity.

When $R_1$ is $C_{1-6}$ alkoxy or $C_{1-6}$ alkylthio and $R_2$ is hydrogen, suitable examples of $R_1$ include methoxy, ethoxy and n- and iso-propoxy, methylthio, ethylthio and n- and iso-propylthio. Preferably $R_1$ is methoxy.

Suitable examples of $R_2/R_{11}$ include methoxy, ethoxy, n- and iso-propoxy, methyl, ethyl, n- and iso-propyl and hydroxy.

Preferred $R_2/R_{11}$ groups include methoxy.

It is generally preferred that $R_{11}$ is in the 4-position relative to the azabicyclylaminocarbonyl side-chain taken as 1, for greater activity in the relevant compound of the formula (I). Particularly preferred groups $R_{11}$ include 4-methoxy.

When $R_1$ and $R_2$ together are $C_{1-3}$ alkylenedioxy, they are favourably methylenedioxy or ethylenedioxy, preferably ethylenedioxy. Suitable examples of $R_{11}$ then include hydrogen, chlorine, bromine, amino, formylamino, acetylamino, propionylamino, n- and iso-butyrylamino, amino substituted by one or two methyl, ethyl, n- or iso-propyl, n-, sec- or tert-butyl cyclohexyl, phenyl or benzyl groups or N-disubstituted by $C_4$ or $C_5$ polymethylene, nitro, methoxy, ethoxy n- and iso-propoxy, methylthio, ethylthio, n- and iso-propylthio and hydroxy.

Preferred $R_{11}$ groups include hydrogen, halogen e.g. chloro and amino. It is generally preferred that $R_{11}$ is in the 4-position relative to the azabicyclylaminocarbonyl side-chain taken as 1, for greater activity in the relevant compound of the formula (I). Particularly preferred groups $R_{11}$ include hydrogen, 4-halo, such as 4-chloro and 4-amino.

Examples of $R_{12}$ $C_{1-6}$ alkylsulphonyl groups include methyl, ethyl and n- and iso-propylsulphinyl. $R_{12}$ is favourably methyl or ethyl, in particular methyl.

It is generally preferred that $R_{12}$ is in the 5-position relative to azabicyclylaminocarbonyl side-chain taken as 1, for greater activity in the relevant compound of the formula (I). Favourably $R_{12}$ is 5-methyl or 5-ethylsulphonyl, preferably 5-methylsulphonyl.

n is preferably 0, q is suitably 0 to 1, preferably 1, p is suitably 0 to 1, preferably 0.

A minimum of 2 or 3 carbon atoms, preferably 3, generally separates the amide and side-chain nitrogen atoms.

When the separation is 3 atoms and n is 0, the $CONR_5$ moiety is preferably in an equatorial orientation to the bicyclic system.

The pharmaceutically acceptable salts of the compounds of the formula (I) include acid addition salts with conventional acids such as hydrochloric, hydrobromic, phosphoric sulphuric, citric, tartaric, lactic and acetic acid.

The pharmaceutically acceptable salts of the compounds of the formula (I) also include quaternary ammonium salts. Examples of such salts include such compounds quaternised by compounds such as $R_9-Y$ wherein $R_9$ is $C_{1-6}$ alkyl, phenyl—$C_{1-6}$ alkyl or $C_{5-7}$ cycloalkyl, and Y is an anion of an acid. Suitable examples of $R_9$ include methyl, ethyl and n- and iso-propyl; and benzyl and phenylethyl. Suitable examples of Y include the halides such as chloride, bromide and iodide.

Examples of pharmaceutically acceptable salts also include internal salts such as N-oxides.

The compounds of the formula (I) can also form hydrates, and the invention extends to such hydrates.

There is a group of compounds within formula (I) wherein:

$R_1$ is $C_{1-6}$ alkoxy or $C_{1-6}$ alkylthio;
$R_2$ is hydrogen; and
$R_{11}$ is $C_{1-6}$ alkoxy, hydroxy or nitro, or
$R_1$ and $R_2$ together are $C_{1-3}$ alkylenedioxy; and
$R_{11}$ is hydrogen, halogen, $CF_3$, $C_{1-7}$ acyl, amino, $C_{1-7}$ acylamino, aminocarbonyl optionally substituted by one or two $C_{1-6}$ alkyl groups, $C_{1-6}$ alkoxy, hydroxy or nitro, and the remaining variables are as defined in formula (I).

A preferred group of compounds within those of the formula (I) which is of interest is of the formula (II):

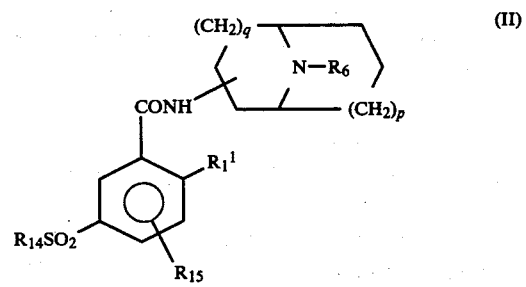

wherein:

$R_1{}^1$ is $C_{1-6}$ alkoxy;
$R_6$, p and q are as defined in formula (I);
$R_{14}$ is $C_{1-6}$ alkyl; and
$R_{15}$ is $C_{1-6}$ alkoxy, $C_{1-6}$ alkyl or hydroxy.

Suitable and preferred $R_1'$ and $R_{15}$ are as so described for the relevant $R_1$ and $R_{11}$ under formula (I). $R_{15}$ is preferably methoxy. The 2,3- and 2,4-dimethoxy nuclei are preferred.

It is preferred that the CONH moiety is in the β-orientation to the bicyclic ring system.

More suitably p is 0 or 1, it is believed preferably 0. Preferably q is 1 and the —CONH— moiety is then attached at the 3-position (standard numbering) in the β-orientation to the bicyclic ring system.

Suitable and preferred $R_6$ are as so described under formula (I). Preferred $R_6$ include $C_{5-7}$ alkyl and cyclohexylmethyl. Particularly preferred $R_6$ include benzyl optionally substituted as defined in formula (I). Unsubstituted benzyl is especially preferred.

A sub-group of compounds within those of formula (II) of interest is of formula (III):

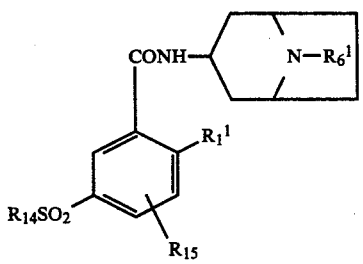

(III)

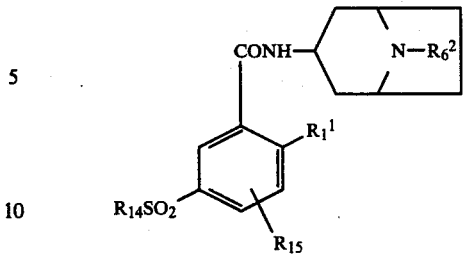

(VI)

wherein:
$R^1_6$ is $C_{1-4}$ alkyl; and
$R_{14}$ and $R_{15}$ are as defined in formula (II).

Suitable and preferred $R^1_6$ are as so described under formula (I) for $R_6$ $C_{1-4}$ alkyl.

It is preferred that the —CONH— moiety is in the β-orientation to the nortropane ring.

A second sub-group of compounds within those of formula (II) of interest is of formula (IV):

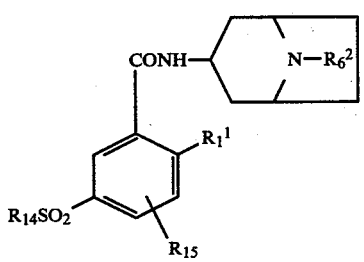

(IV)

wherein:
$R^2_6$ is $C_{5-7}$ alkyl; a group —$(CH_2)_t R^1_8$ wherein t is 1 or 2 and $R^1_8$ is optionally substituted phenyl as defined in formula (I); cyclohexylmethyl, or 2-thienylmethyl.

Suitable and preferred $R^2_6$ are as so described for the corresponding $R_6$ groups under formula (I).

$R^2_6$ benzyl is especially preferred.

It is preferred that the —CONH— moiety is in the β-orientation to the nortropane ring.

A third sub-group of compounds within those of formula (II) of interest is of formula (V):

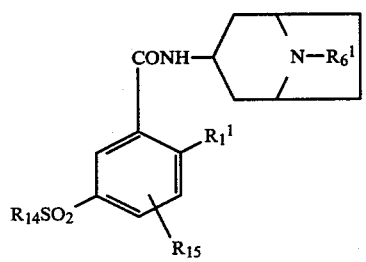

(V)

wherein:
$R^1_6$ is as defined in formula (III) and
$R_{14}$ and $R_{15}$ are as defined in formula (II).

Suitable and preferred $R^1_6$ are as so described under formula (III). Suitable and preferred $R_{14}$ and $R_{15}$ are as so described under formula (II).

A fourth sub-group of compounds within those of formula (II) of interest is of formula (VI):

wherein:
$R^2_6$ is as defined in formula (IV) and
$R_{14}$ and $R_{15}$ are as defined in formula (II).

Suitable and preferred $R^2_6$ are as so described under formula (IV). Suitable and preferred $R_{14}$ and $R_{15}$ are as so described under formula (II).

A second group of compounds of the formula (I) is of the formula (VII):

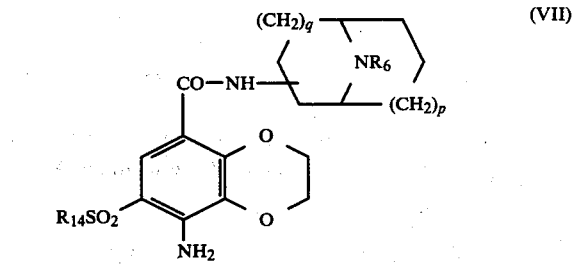

(VII)

wherein:
the variables are as defined in formula (II).

Suitable and preferred $R_{14}$ are as so described under formula (II).

More suitable p is 0 or 1, it is believed preferably 0. Preferably q is 1 and the moiety of formula (III) is then attached at the 3-position (conventional numbering) and in the β-orientation).

Suitable and preferred examples of $R_6$ in formula (VI) include those listed under formula (I) for $R_6$. Preferred examples of $R_6$ include $C_{5-7}$ alkyl and cyclohexylmethyl. Particularly preferred examples of $R_6$ also include benzyl optionally substituted in the phenyl ring as defined under formula (I). Unsubstituted benzyl is especially preferred.

A sub-group of compounds within those of formula (VI) are those of the formula (VIII):

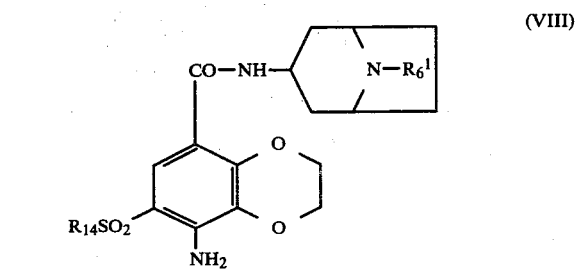

(VIII)

wherein:
$R^1_6$ is $C_{1-4}$ alkyl.

Suitable examples of $R^1_6$ are as so described for $R_6$ $C_{1-4}$ alkyl under formula (I).

It is preferred that the —CONH— moiety is in the β-orientation to the nortropane ring.

A particularly preferred sub-group of compounds within those of formula (VI) are those of the formula (IX):

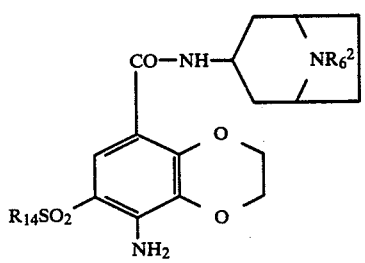

wherein $R^2_6$ is $C_{5-7}$ alkyl; a group $-(CH_2)_t R^1_8$ wherein t is 1 or 2 and $R^1_8$ is optionally substituted phenyl as defined in formula (I); cyclohexylmethyl, or thienylmethyl.

Suitable and preferred $R^2_6$ are as so described for the corresponding $R_6$ groups under formula (I).

$R^2_6$ benzyl is especially preferred.

It is preferred that the —CONH— moiety is in the β-orientation to the nortropane ring.

A sub-group of compounds within those of the formula (VII) of interest are those of the formula (X):

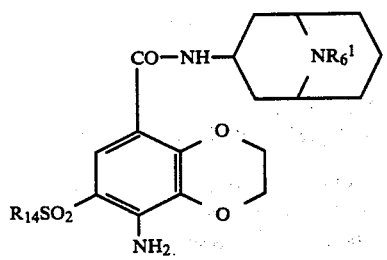

wherein $R^1_6$ is as defined in formula (III).

Suitable examples of $R^1_6$ are as so described under formula (III).

Another sub-group of compounds within those of the formula (VII) of interest are those of the formula (XI):

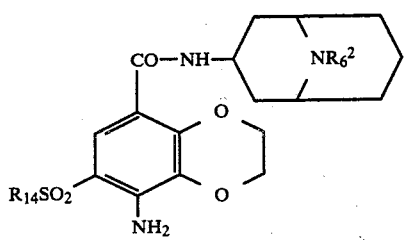

wherein:
$R^1_6$ is as defined in formula (VIII).

Suitable and preferred examples of $R^1_6$ are as so described under formula (VIII).

A preferred third group of compounds within those of the formula (I) which is of interest is of the formula (XII):

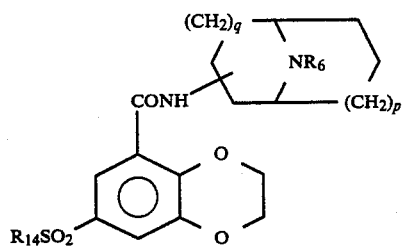

wherein:
the variables are as defined in formula (II).

Suitable and preferred $R_{14}$ are as so described for alkyl groups of $R_{12}$ $C_{1-6}$ alkyl sulphonyl under formula (I).

It is preferred that the CONH moiety is in the β-orientation to the bicyclic ring system.

More suitably p is 0 or 1, it is believed preferably 0. Preferably q is 1 and the —CONH— moiety is then attached at the 3-position (standard numbering) in the β-orientation to the bicyclic ring system.

Suitable and preferred $R_6$ are as so described under formula (I). Preferred $R_6$ include $C_{5-7}$ alkyl and cyclohexylmethyl. Particularly preferred $R_6$ include benzyl optionally substituted as defined in formula (I). Unsubstituted benzyl is especially preferred.

A sub-group of compound within those of formula (XII) of interest is of formula (XIII):

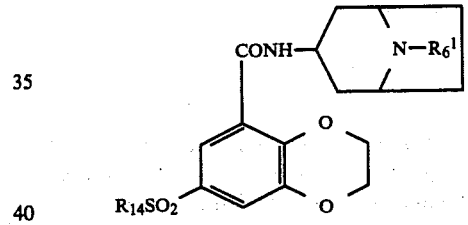

wherein:
$R^1_6$ is as defined in formula (III) and
$R_{14}$ is as defined in formula (II).

Suitable and preferred $R^1_6$ are as so described under formula (III). Suitable and preferred $R_{14}$ are so described under formula (II).

A second sub-group of compounds within those of formula (XII) is of formula (XIV):

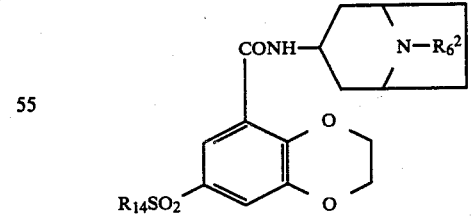

wherein:
$R^2_6$ is as defined in formula (IV) and
$R_{14}$ is as defined in formula (II).

Suitable and preferred $R^2_6$ are as so described under formula (IV). Suitable and preferred $R_{14}$ and $R_{15}$ are as so defined under formula (II).

A third sub-group of compounds within those of formula (XII) of interest is of formula (XV):

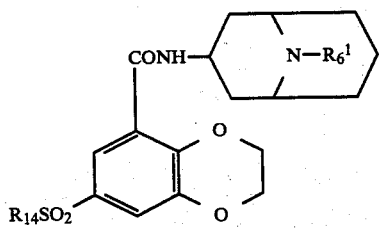

(XV)

wherein:

$R^1_6$ is as defined in formula (III) and $R_{14}$ is as defined in formula (II)

Suitable and preferred $R^1_6$ are as so described under formula (III). Suitable and preferred $R_{14}$ and $R_{15}$ are as so described under formula (II).

A fourth sub-group of compounds within those of formula (XII) of interest is of formula (XVI):

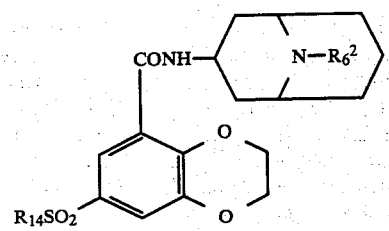

(XVI)

wherein:

$R^2_6$ is as defined in formula (IV) and $R_{14}$ is as defined in formula (II).

Suitable and preferred $R^2_6$ are as so described under formula (IV). Suitable and preferred $R_{14}$ are as so described under formula (II).

A fourth group of compounds within those of formula (I) is of formula (XVII):

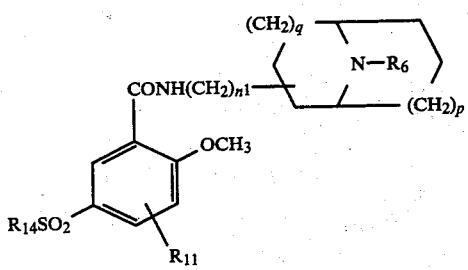

(XVII)

wherein $n^1$ is 1 or 2 and the remaining variables are as defined in formula (II).

More suitably p and q are each 0 or 1.

Preferably p is 0 and q is 1. Preferably $n^1$ is 1.

Suitable and preferred $R_6$, $R_{11}$ and $R_{14}$ are as so described under formulae (I) and (II).

A fifth group of compounds within those of formula (I) is of formula (XVIII):

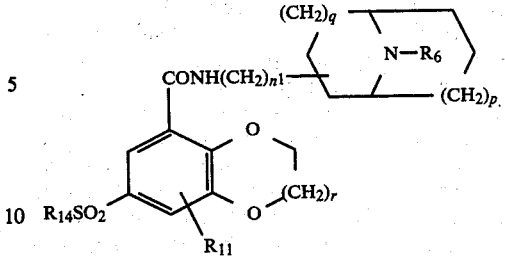

(XVIII)

wherein $n^1$ is 1 or 2 and the remaining variables are as defined in formula (II).

More suitably p and q are each 0 or 1.

Preferably p is 0 and q is 1. Preferably $n^1$ is 1.

Suitable and preferred $R_6$, $R_{11}$ and $R_{14}$ are as so described under formulae (I) and (II).

It will of course be realised that the compounds of the formula (I) have chiral or prochiral centres, and thus are capable of existing in a number of stereoisomeric forms. The invention extends to each of these stereoisomeric forms, and to mixtures thereof (including racemates). The different stereoisomeric forms may be separated once from the other by the usual methods, or any given isomer may be obtained by stereospecific or asymmetric synthesis.

The compounds of formula (I) may be prepared in analogous manner to the compounds of formula (A).

The invention thus provides a process for the preparation of a compound of the formula (I), which process comprises reacting an acid of the formula (XIX):

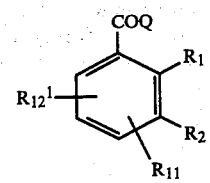

(XIX)

wherein Q is a leaving group; $R_{11}$ is as defined; and $R^1_{12}$ is $C_{1-6}$ alkylsulphonyl or, when $R_1$ is $C_{1-6}$ alkoxy, $C_{1-6}$ alkylthio; with a compound of formula (XX):

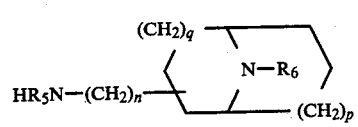

(XX)

variable groups being as defined in formula (I); and thereafter if necessary converting a group $R_{11}$ or $R_{12}$ in the thus formed compound to another group $R_{11}$ or $R_{12}$ respectively; converting $R_6$ to another $R_6$; and optionally forming a pharmaceutically acceptable salt of the resultant compound of the formula (I).

The leaving group Q is a group readily displaceable by a nucleophile. Suitable examples of Q are hydroxy, halogen such as chloro and bromo and acyloxy such as $C_{1-4}$ hydrocarbyloxy such as pentachlorophenoxy.

If a leaving group is hydroxy, then the reaction is preferably carried out in an inert non-hydroxylic solvent, such as benzene, toluene or diethyl ether in the presence of a dehydrating catalyst, such as a carbodiimide, for example dicyclohexylcarbodiimide. The reaction may be carried out at a non-extreme temperature such as $-10°$ to $100°$ C., for example $0°$ to $80°$ C.

If a leaving group is a halide, then the reaction is preferably carried out at a non-extreme temperature in an inert non-hydroxylic solvent, such as benzene, toluene or diethyl ether. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate.

If a leaving group is acyloxy, then the reaction is preferably carried in substantially the same manner as if the leaving group were hydroxy. Suitable examples of acyloxy leaving groups include $C_{1-4}$ alkanoyloxy, mesyloxy, tosyloxy and triflate.

If a leaving group is $C_{1-4}$ alkoxycarbonyloxy, then the reaction is preferably carried out in an inert solvent, such as methylenechloride at a non-extreme temperature in the presence of an acid acceptor, such as triethylamine.

If a leaving group is activate hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

The intermediates of the formulae (XIX) and (XX) are either known compounds or can be prepared by analogous processes to known compounds.

It will be realised that in the compound of the formula (I) the —CO—NR$_5$—(CH$_2$)$_n$— linkage may have an $\alpha$ or $\beta$ orientation with respect to the ring of the bicyclic moiety to which it is attached. A mixture of $\alpha$ and $\beta$ isomers of the compound of the formula (I) may be synthesised non-stereospecifically and the desired isomer separated conventionally therefrom, e.g. by chromatography; or alternatively the $\alpha$ or $\beta$ isomer may if desired be synthesised from the corresponding $\alpha$ or $\beta$ form of the compound of the formula (XX).

Synthesis from the corresponding $\alpha$ or $\beta$ isomer of the compound of the formula (XX) is in general preferred.

The $\alpha$ or $\beta$ form of the compound of the formula (XX) may if desired be prepared by known stereospecific processes, such as those leading to the $\alpha$ and $\beta$ isomers of the compound of the formula (XX) depicted in the Scheme and described in Descriptions 3C, 4A and 4C of European Patent Application No. 79302978.6 and allowed U.S. patent application No. 107,413 for the $\alpha$-isomers and Descriptions 2 and/A and B of these Applications for the $\beta$-isomers.

The precursor of the compound of the formula (XX) may be stereospecifically synthesised, such as the azide (D3) of Description 2 of the above European Application and U.S. Patent and present Description 1, and then converted to the corresponding desired isomer of the compound of the formula (XX) under non-stereospecific conditions with retention of configuration. Alternatively, the precursor may itself have no (pro)chiral centre at the relevant position, such as the oximes and imines of Descriptions 3 and 4 of the above European and U.S. Applications but be converted under stereospecific conditions to the desired isomer of the compound of the formula (XX).

Alternatively, a mixture of the $\alpha$ and $\beta$ isomers of the compound of the formula (XX) may be synthesised non-stereospecifically and the desired isomer separated conventionally therefrom e.g. by chromatography. However, in this case it is generally more convenient to react the mixture to give a mixture of $\alpha$ and $\beta$ isomers of the compound of the formula (I) and to separate these if desired as hereinbefore described.

The following Scheme 1 illustrates stereospecific and non-stereospecific synthetic routes to intermediates of the formula (XX) wherein n is 0.

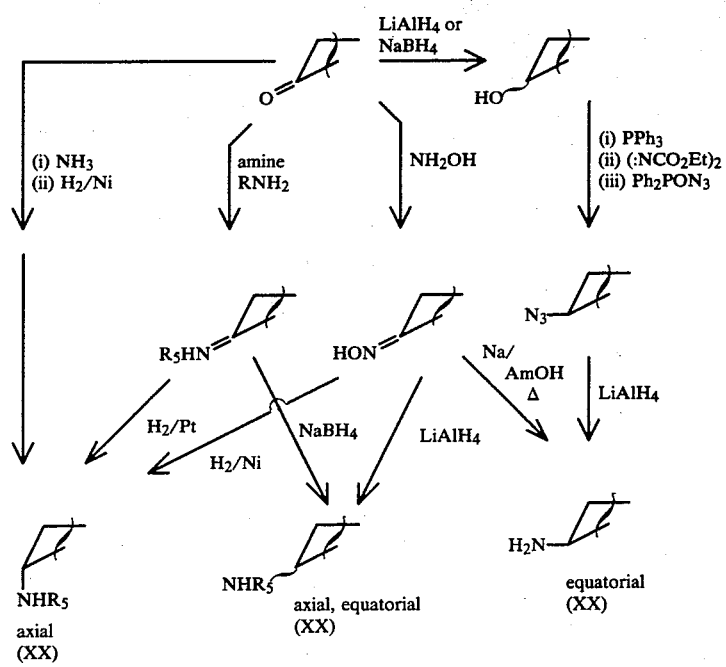

(Remainder of ring system omitted for clarity)

The following Scheme 2 illustrates preparative routes to intermediates of the formula (XX) wherein n is 1 or 2.
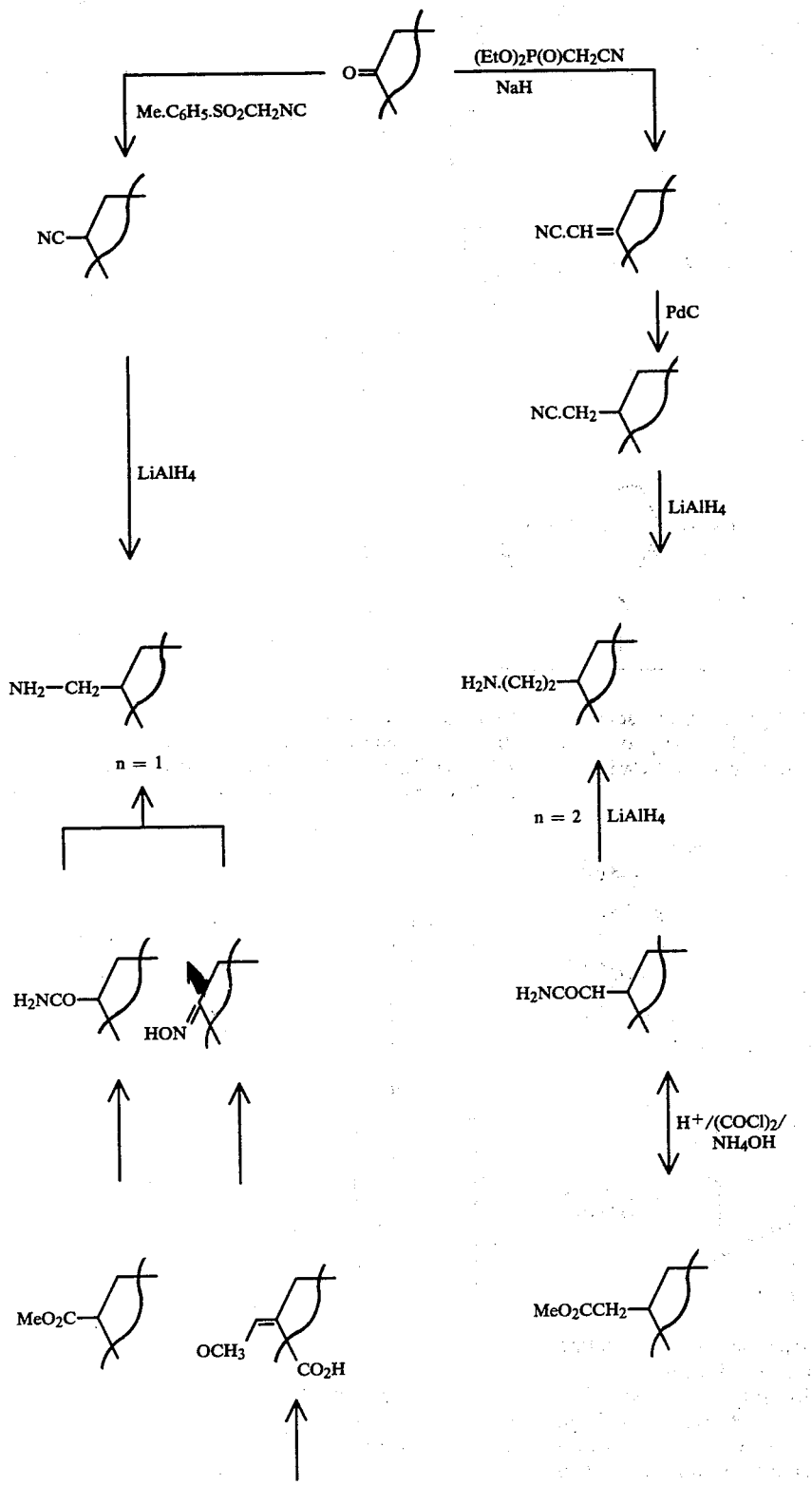

-continued

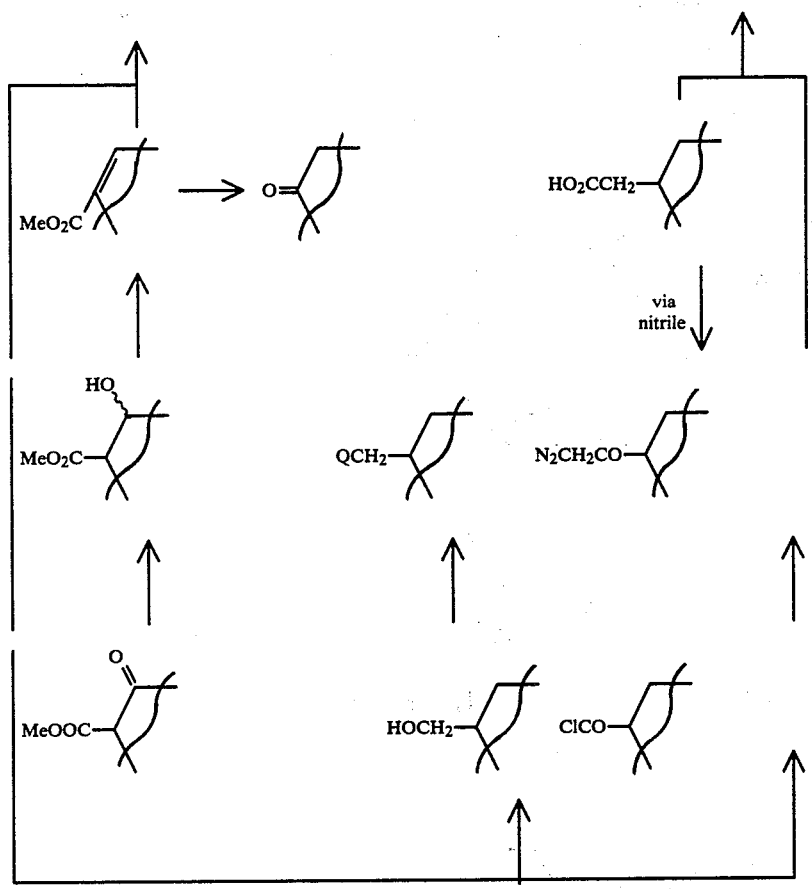

Introduction of the functional group $R_{12}$ in acids of formula (XX), can be achieved by chlorosulphonation followed by reduction, basic cleavage and alkylation as shown in scheme 1:

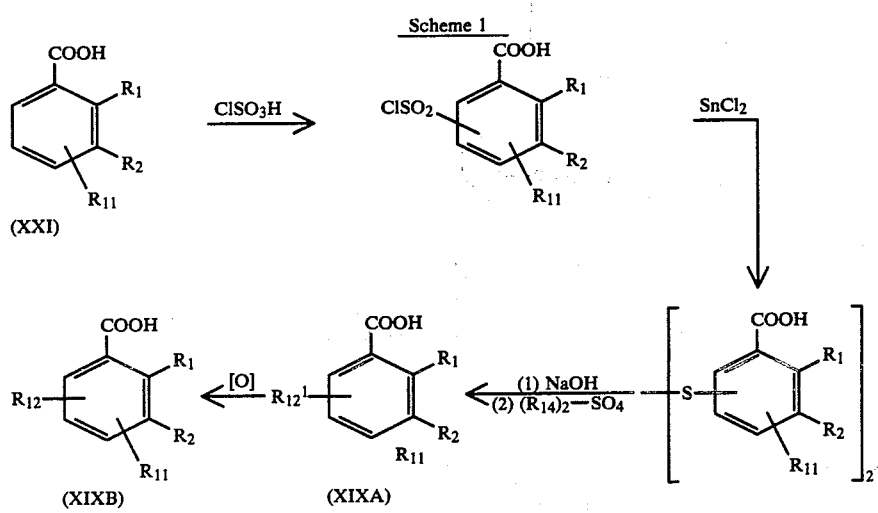

The process of chlorosulphonation involves reacting chlorosulphonic acid with an acid of formula (XXI) to give the corresponding chlorosulphonyl derivative. Reduction of the chlorosulphonyl derivative with tin (II) chloride in hydrochloric acid will give the disulphide, which may be hydrolysed by heating with 10% sodium hydroxide solution to give a thiol. The thiol can be reacted in situ with an alkylating agent such as a dialkyl sulphate resulting in the formation of the alkyl sulphide (XIXA). If desired compounds of the formula (XIXB) may be formed by oxidation of the alkylthio derivatives (XIXA). Suitable reagents for these oxidations include hydrogen peroxide and acetic acid; sodium periodate or potassium hydrogen persulphate. Other methods which may be used to form the alkyl sulphides (XIXA) include the treatment of acids of formula (V) with perchloric acid, phosphonyl chloride and dimethyl sulphoxide to form the corresponding sulphonium salts (IX), followed by demethylation with potassium chloride as outlined in scheme 2.

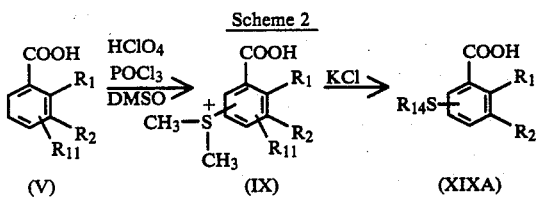

or the thiocyanation of the esters of acids of formula (XXI) using sodium or potassium thiocyanate followed by base hydrolysis and alkylation as shown in scheme 3.

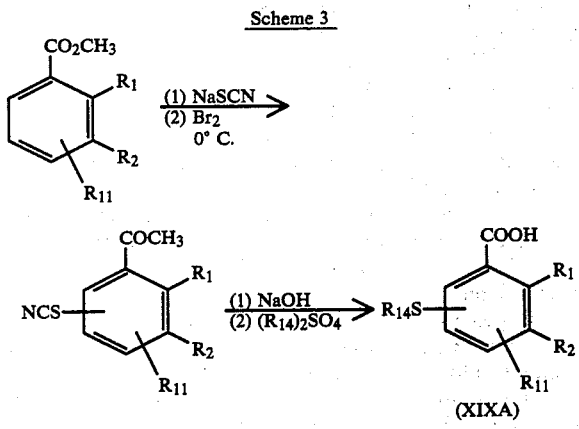

When $R_1$ is $C_{1-6}$ alkoxy or $C_{1-6}$ alkylthio, acids of the formula (XXI) are known compounds, or prepared by analogy with known compounds.

When $R_1$ and $R_2$ together are $C_{1-3}$ alkylenedioxy, formation of the alkylenedioxy bridge in acids of formula (XXI) may be carried out by heating an acid of formula (XXII) with a dibromoalkane in the presence of an inorganic base such as potassium hydroxide or potassium carbonate using ethanol-water as the solvent.

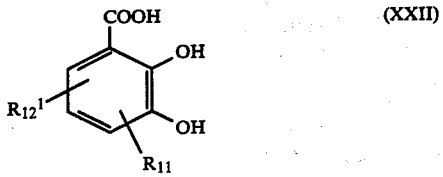

Compounds of the formula (XXII) are known compounds or prepared by analogy with known compounds.

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_9Y$ as defined. This reaction is suitably carried out in an appropriate solvent such as acetone, methanol, ethanol, dimethylformamide, at ambient or raised temperature and pressure. The nitrogen atom of the bicyclic moiety may also form an N-oxide to give an internal N-oxide salt of the compound of the formula (I). The N-oxides may be prepared in conventional manner such as by reaction of the chosen compound of the formula (I) with an organic per-acid, such as m-chloroperbenzoic acid. This reaction is suitably carried out at below-ambient temperature in an organic solvent, preferably a chlorinated hydrocarbon solvent.

It will be apparent that the product of the reaction of the compounds of formulae (XIX) and (XX) will be of formula (XXII):

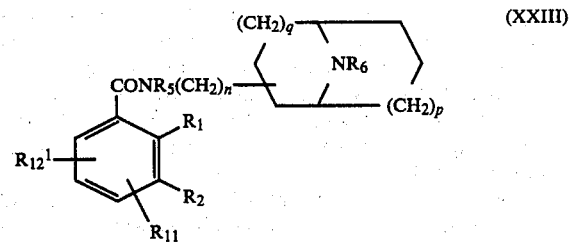

wherein the variables are as defined in formulae (XIX) and (XXII). Compounds of the formula (XXII) containing an $R_{11}$ or $R^1_{12}$ group convertible to $R_{11}$ or $R_{12}$ are useful intermediates and as such form an important aspect of the invention. Some compounds of the formula (XXII) will also fall within formula (I).

Compounds of the formula (I) containing an $R_{11}$, or $R_6$ group which is convertible to another $R_{11}$, $R_6$ group are also useful intermediates and as such form an important aspect of the invention.

The skilled man will appreciate that the choice or necessity of conversion of groups $R_{11}$, $R_{12}^1$, or $R_6$ as above will be dictated by their nature and position.

By way of example of such conversions, the conversion of a $R_{11}$ nitro group to a $R_{11}$ amino group may be achieved in conventional manner such as by reduction. Thus an optional process step provided by this invention in the preparation of the compounds of the formula (I) wherein $R_{12}$ is an amino group comprises the reduction of a corresponding intermediate of formula (XXII) wherein $R_{12}$ is a nitro group.

The reduction of the intermediates wherein $R_{12}$ is a nitro group may be effected with reagents known to be suitable for reducing nitroanisole to aminoanisole. A suitable reagent for this reduction is stannous chloride in hydrochloric acid or in mixtures of hydrochloric and acetic acid. The desired amino compound may be obtained from the reaction mixture by respectively neutralisation followed by extraction into a water immiscible solvent such as ethyl acetate from which it may be recovered by evaporation of the solvent.

Another suitable method is catalytic hydrogenation at atmospheric pressure in polar solvent such as ethanol. Transition metal catalysts such as Raney nickel are often used. The desired compound may be obtained from the reaction mixture by filtration and evaporation to dryness.

The initial crude product in both cases may be purified by chromatography or crystallisation or by forming an acid addition salt which may be recrystallised.

In general however, it is more convenient to prepare a compound of the formula (I) wherein $R_{12}$ is an amino group from the corresponding $C_{1-7}$ acylamino acid or its reactive derivative, and to deacylate the compound of the formula (I) so formed.

Those compounds of the invention wherein $R_{11}$ or $R^1{}_{11}$ is a $C_{1-7}$ acylamino group may be prepared from the corresponding intermediate wherein $R_{11}$ or $R^1{}_{11}$ is an amino group by reaction with an acylating derivative, such as previously described as a suitable acylating derivative, e.g. of the acid of the formula (XIX). The reaction may proceed as described for the reaction of the compounds of the formula (I). For an $R_{11}$ formamido group acylation may be effected with the free acid.

This invention thus also provides an optional process for the preparation of a compound of the formula (I) wherein $R_{11}$ is an amino group which process comprises the deacylation of a corresponding intermediate wherein $R_{11}$ or $R^1{}_{11}$ is a $C_{1-7}$ acylamino group.

Generally the hydrolysis reaction may be effected by treatment with a base such as an alkali metal hydroxide.

Although as noted $R^1{}_{11}$ may be nitro, it is generally preferred that $R^1{}_{11}$ is a $R_{11}$ group.

It will be appreciated that, when $R_6$ in the compound of the formula (XXIII) is optionally substituted benzyl as hereinbefore defined, $R_6$ may be replaced by another group $R_6$.

Such $R_6$ benzyl groups may be removed by conventional transition metal catalysed hydrogenolysis to give compounds of the formula (XXIV):

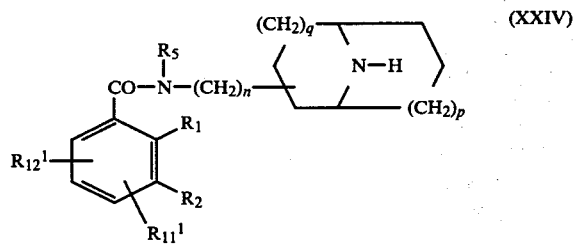

wherein the variable groups are as defined in formulae (XIX) and (XX).

This invention also provides an optional process step in the preparation of a compound of the formula (I) which comprises the reaction of a corresponding compound of the formula (XXIII) as hereinbefore defined with a compound $Q_2R_6$ wherein $R_6$ is as defined in formula (I) and $Q_2$ is a group or atom readily displaced by a nucleophile, converting $R^1{}_{12}$ and $R^1{}_{11}$ in the resulting compound of formula (XIV) to $R_{12}$ and another $R_{11}$ respectively and optionally forming a pharmaceutically acceptable salt of the resulting compound of the formula (I).

Suitable values for $Q_2$ include Cl, Br, I, $OSO_2CH_3$ or $OSO_2C_6H_4pCH_3$.

Favoured values for $Q_2$ include Cl, Br and I.

Particularly suitably the compound $Q_2R_6$ is a benzyl halide such as benzyl bromide or benzyl chloride.

The reaction may be carried out under conventional alkylation conditions for example in an inert solvent such as dimethylformamide in the presence of an acid acceptor such as potassium carbonate. Generally the reaction is carried out at a non-extreme temperature such as at ambient or at a slightly elevated temperature.

However, it is generally more convenient to interconvert $R_6$ in the compound of the formula (XIX) before coupling with the compound of the formula (XX) or its derivative. Such interconversions are effected conveniently under the above conditions. It is desirable to protect the amine function with a group readily removable by acidolysis such as a $C_{2-7}$ alkanoyl groups before $R_6$ interconversion.

$R^1{}_{12}$ $C_{1-6}$ alkylthio may be converted to $R_{12}$ as defined.

An alternative process according to the present invention thus comprises oxidising a compound of the formula (XXIII) as hereinbefore defined wherein $R_1$ is $C_{1-6}$ alkoxy and $R^1{}_{12}$ is $C_{1-6}$ alkylthio and thereafter if necessary converting a group $R^1{}_{11}$ or $R_6$ in the thus formed compound to a group $R_{11}$ or $R_6$ as hereinbefore defined; and optionally forming a pharmaceutically acceptable salt of the resultant compound of the formula (I).

These oxidations may conveniently be carried out conventionally at below ambient temperatures using an organic peracid in a non-aqueous inert reaction medium preferably a chlorinated hydrocarbon solvent, for example using 3-chloroperbenzoic acid, or using a water soluble inorganic strong oxidant, such as an alkali metal permanganate, periodate or hydrogen peroxide in aqueous solution.

It will be appreciated by the skilled man that, depending on the other specific substituents in the compound of the formula (I), such an oxidation on a compound of the formula (I) may also form the N-oxide of the bicyclic moiety therein.

Given the specific substitution desired and having been decided whether the compound or its N-oxide is required, the skilled man will readily ascertain whether such interconversion is desirable.

In general however it is more convenient to prepare a compound of formula (I) from the corresponding $C_{1-6}$ alkylsulphinyl acid or its reactive derivative.

Any conversion of $R_{11}$, $R_{12}{}^1$, $R_{12}$, or $R_6$ may take place in any desired or necessary order.

The compounds of the formula (I) are dopamine antagonists.

Depending on their balance between peripheral and central action, the compounds of the formula (I) may be used in the treatment of disorders related to impaired gastro-intestinal motility, such as retarded gastric emptying, dyspepsia, flatulence, oesophagal reflux, peptic ulcer and emesis, and/or in the treatment of disorders of the central nervous system, such as psychosis.

All the compounds of the formula (I) may be used in the treatment of emesis.

The quaternary salts of the compounds of formula (I) are of interest for their beneficial effect on gastric motility.

The invention therefore also provides a pharmaceutical composition comprising a compound of the formula (I), or a hydrate or a pharmaceutically acceptable salt thereof, together with a pharmaceutically acceptable carrier. Such compositions may be adapted for oral or parenteral administration, and as such may be in the form of tablets, capsules, oral liquid preparations, powders, granules, lozenges, reconstitutable powders, injectable and infusable solutions or suspensions; the compositions may also be in the form of suppositories. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agents, emulsifying agents, non-aqueous vehciles (which may include edible oils), preservatives, and if desired conventional flavouring or colouring agents.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of maladies in mammals including humans comprising the administration of an effective amount of a compound of the formula (I) or a pharmaceutically acceptable salt thereof to the sufferer. The "effective amount" will depend in the usual way on a number of factors such as the nature and severity of the malady to be treated, the weight of the sufferer, and the actual compound used.

However by way of illustration, unit doses will suitably contain 0.01 to 20 mgs of the compound of formula (I), for example 0.02 to 10 mgs.

Again by way of illustration, such unit doses will suitably be administered more than once a day, for example 2, 3, 4, 5 or 6 times a day, in such a way that the total daily dose is suitably in the range 0.001 to 10 mg/kg per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the preparation of compounds of formula (I), and the following Descriptions illustrate the preparation of intermediates therefor.

DESCRIPTION 1

2,3-Ethylenedioxybenzoic acid (D1)

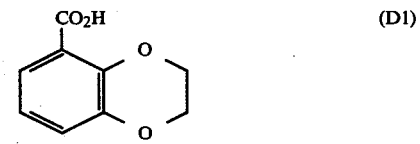

2,3-Dihydroxybenzoic acid (25 g, 0.16 mol) was heated under reflux in an oxygen-free atmosphere with potassium hydroxide (26.42 g, 0.47 mole) and dibromoethane (13.46 g, 0.07 mol) using 95% ethanol (60 ml) and water (142 ml as solvent as described in J. Org. Chem. (1948), 13, 489–95 to give 2,3-ethylenedioxybenzoic acid (12.2 g, 43%), m.pt. 195°–196° C.

DESCRIPTION 2

5-Chlorosulphonyl-2,3-ethylenedioxybenzoic acid (D2)

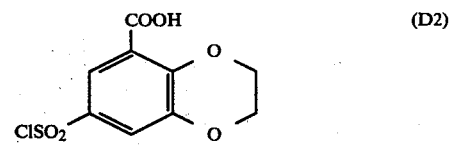

2,3-Ethylenedioxybenzoic acid (3.4 g) was added in small portions to chlorosulphoric acid (5 ml) keeping the temperature of the mixture below 5° C. The reaction mixture was then warmed to 55° C. and maintained at this temperature for 2 hours before cooling and pouring into ice-water. The precipitated product was filtered and dried in vacuo to give 5-chlorosulphonyl-2,3-ethylenedioxybenzoic acid (4.1 g, 79%), m.pt. 210°–214° C.

DESCRIPTION 3

Bis(2,3-ethylenedioxybenzoic acid)5-disulphide (D3)

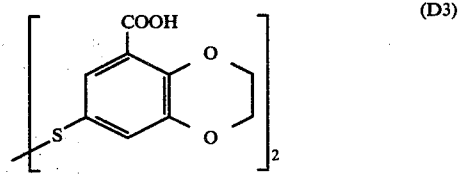

Tin (11) chloride (38 g, 0.168 mol) was added in portions to a suspension of 5-chlorosulphonyl-2,3-ethylenedioxybenzoic acid (8 g, 0.028 mol) in a mixture of concentrated hydrochloric acid (18 ml) and water (6 ml) and the mixture was stirred for 4 hours. The reaction mixture was filtered, washed with 5N hydrochloric acid and dried over potassium hydroxide in vacuo to give bis(2,3-ethylenedioxybenzoic acid)5-disulphide (9 g).

DESCRIPTION 4

2,3-Ethylenedioxy-5-methylthiobenzoic acid (D4)

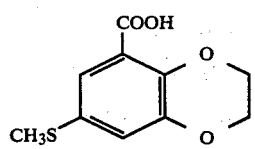
(D4)

The disulphide (D3) (9 g) was heated under reflux in 10% sodium hydroxide solution (150 mls) for 1 hour, before filtration of the hot solution. The filtrate was allowed to cool before the addition of dimethyl sulphate (4 ml). After standing at room temperature overnight the solution was acidified with 5N hydrochloric acid, filtered and dried over potassium hydroxide in vacuo to give 2,3-ethylenedioxy-5-methylthiobenzoic acid (2.4 g 39%), m.pt. 181°–183° C.

DESCRIPTION 5

2,3-Ethylenedioxy-5-methylsulphonylbenzoic acid (D5)

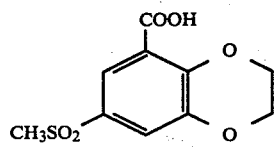
(D5)

2,3-Ethylenedioxy-5-methylthiobenzoic acid (2.4 g, 0.01 mol) and glacial acetic acid (90 ml) were warmed to 40° C. before the dropwise addition of hydrogen peroxide (100 vol., 6.6. ml). The mixture was stirred at 80° C. for 4 hours, cooled and poured onto ice-water to give a precipitate which was filtered and dried to give 2,3-ethylenedioxy-5-methylsulphonylbenzoic acid (1.3 g, 50%), m.pt. 247°–249° C.

DESCRIPTION 6

5-Chlorosulphonyl-2,4-dimethoxybenzoic acid (D6)

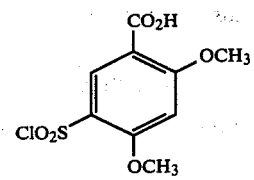
(D6)

Using the method of Description 2, chlorosulphonation of 2,4-dimethoxybenzoic acid gave the title compound in 71% yield.

DESCRIPTION 7

Bis(2,4-dimethoxybenzoic acid)5-disulphide (D7)

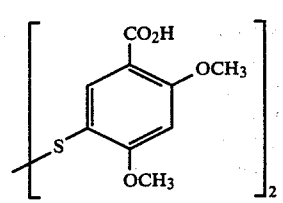
(D7)

Using the method of Description 3, 5-chlorosulphonyl-2,4-dimethoxybenzoic acid gave the title compound.

DESCRIPTION 8

2,4-Dimethoxy-5-methylsulphonylbenzoic acid (D8)

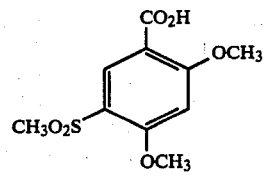
(D8)

Using the method of Description 5, 2,4-dimethoxy-5-methylthiobenzoic acid (D7) gave the title compound in 98% yield. m.p. 292°–292.5° C.

DESCRIPTION 9

2,4-Dimethoxy-5-methylthiobenzoic acid (D9)

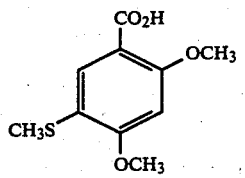
(D9)

Using the method of Description 4, bis(2,4-dimethoxybenzoic acid)-5-disulphide ( ) gave the title compound in 34% yield. m.p. 151°–153° C.

DESCRIPTION 10

5-Chlorosulphonyl-2,3-dimethoxybenzoic acid (D10)

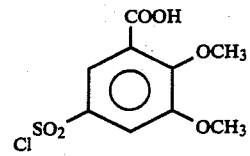
(D10)

2,3-Dimethoxybenzoic acid (5 g) was added in small portions to chlorosulphonic acid (10 mls) keeping the temperature of the mixture below 5° C. The reaction mixture was then warmed to 55° C. and maintained at this temperature for 2 hours before cooling and pouring into ice-water.

The precipitated product was filtered and dried in vacuo to give 5-chlorosulphonyl-2,3-dimethoxybenzoic acid (3.8 g, 50%).

DESCRIPTION 11

Bis(2,3-dimethoxybenzoic acid)-5-disulphide (D11)

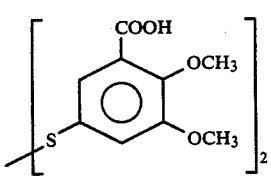
(D11)

Tin (11) chloride (26 g) was added in portions to a suspension of 5-chlorosulphonyl-2,3-dimethoxy-benzoic acid (5.5 g) in a mixture of concentrated hydrochloric acid (13 mls) and water (5 mls) and the mixture was stirred for 4 hours.

The reaction mixture was filtered, washed with 5N hydrochloric acid and dried over potassium hydroxide in vacuo to give bis(2,3-dimethoxybenzoic acid)-5-disulphide (4.2 g).

DESCRIPTION 12

2,3-Dimethoxy-5-methylthiobenzoic acid (D12)

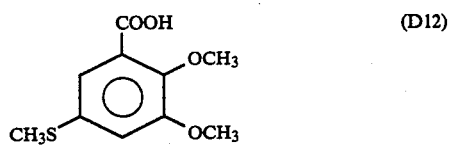

The disulphide (D11) (4.0 g) was heated under reflux in 10% sodium hydroxide solution (100 ml) for 1 hour, before filtration of the hot solution. The filtrate was allowed to cool before the addition of dimethyl sulphate (3 mls). After standing at room temperature overnight the solution was acidified with 5N hydrochloric acid, filtered and dried over potassium hydroxide in vacuo to give 2,3-dimethoxy-5-methylthiobenzoic acid (1.2 g, 28%) m.pt. 139°–141° C.

DESCRIPTION 13

2,3-Dimethoxy-5-methylthio-N[3β(8-benzyl-8-azabicyclo[3.2.1]octyl)]benzamide hydrochloride (D13)

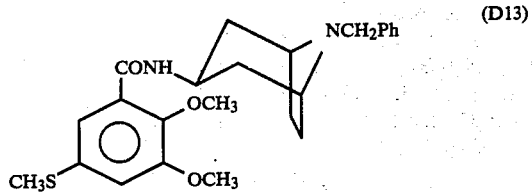

2,3-Dimethoxy-5-methylthiobenzoic acid (1.13 g) was suspended in dry dichloromethane (30 ml) with oxalyl chloride (0.44 ml) and dry dimethylformamide (0.5 ml) added. The mixture was stirred at room temperature until it became homogeneous.

The solution was cooled to 0° C. and kept below this temperature during the dropwise addition of triethylamine (2 ml) in dry dichloromethane (10 ml), followed by the dropwise addition of 3β-amino-8-benzyl-8-acabicyclo[3.2.1]octane (1.0 g) in dry dichloromethane (10 ml).

The reaction mixture was allowed to warm to room temperature before being shaken with 10% sodium hydroxide solution (10 ml). The organic layer was dried over anhydrous sodium sulphate, filtered and the solvent was removed in vacuo to give an oil (2.3 g). Purification by column chromatography (silica, chloroform) gave an oil (1.7 g, 85%) from which the hydrochloride salt was prepared m.pt. 217°–217,5° C., $C_{24}H_{31}N_2SClO_3$ requires C, 62.27; H, 6.7; N, 6.05%. Found C, 62.10; H, 6.76; N, 5.97. nmr ($D_2O$) τ 2.45–2.65 (6H, M, $NCH_2C_6H_5$ and —CONH—), 3.0 (1H, d, aromatic H), 3.1 (1H, d, aromatic H), 5.8 (2H, S, $NCH_2C_6H_5$), 6.0 (2H, M, bridgehead H's), 6.2 (3H, S, —OCH$_3$), 6.3 (3H, S, —OCH$_3$), 7.6–8.35 (11H, S and M, —SCH$_3$ and methylene H's).

DESCRIPTION 14

2-Methoxy-4-methyl-5-methylsulphonylbenzoic acid

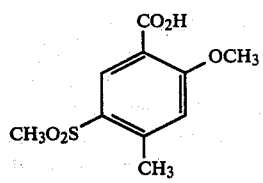

Chlorosulphonic acid (35 ml) was added dropwise, over 2 hours, to a mixture of 4-methyl O-anisic acid (prepared as described by Marc Julia and Mme Francine Chastrelle in Bull. Soc. Chim. Fr. 1962, 2255–2261) (16.6 g, 0.1 mole), dichloroethane (36 ml) and sodium chloride (6 g). The mixture was stirred and warmed to 40° for 1 hour then heated to 65° for 17 hours. Subsequent cooling and pouring into ice-water gave 5-chlorosulphonyl-4-methyl-2-methoxybenzoic acid as colourless microcrystals (25 g, 95%).

The sulphonyl chloride (15.4 g, 0.058 mole) was suspended in concentrated hydrochloric acid (50 ml) and water (30 ml) and treated portionwise, with stirring, with solid stannous chloride hexahydrate (90 g). After stirring for 24 hours, the yellow "plastic" solid was filtered and washed with dilute hydrochloric acid and sucked as dry as possible. Yield 11 g, 96%.

This solid was boiled with 10% sodium hydroxide (110 ml) for ¾ hour, cooled and treated at room temperature with excess dimethylsulphate (34 g, 26 ml). After 24 hours, the solution was made alkaline and heated to reflux for 20 minutes, filtered and acidified to give a white precipitate. This gelatinous precipitate was boiled with toluene (100 ml) and azeotroped to remove occluded water. The toluene was evaporated in vacuo to give 2-methoxy-4-methyl-5-methylthio benzoic acid (30 g; 25%) as colourless microcrystals.

nmr CDCl$_3$ δ: 7.8 (s, 1H, 6Ar—H); 6.75 (s, 1H, 3Ar—H); 4.00 (s, 3H, CH$_3$O—Ar); 2.45 (s, 3H, CH$_3$S—); 2.44 (s, 3H, CH$_3$—Ar);

This acid (3.0 g, 14.2 mmole) was dissolved in glacial acetic acid at 40° C., stirred, and treated dropwise with 100 volume 30% hydrogen peroxide (10 ml). The temperature rose to 80° and was maintained at 80° C. for 6 hours. The mixture was cooled and filtered to give the title compound (3.37 g; 98%) as colourless microcrystals mp 228° nmr d$_6$-DMSO δ: 8.2 (s, 1H, 6Ar—H); 7.2 (s, 1H, 3Ar—H); 3.88 (s, 3H, CH$_3$O—Ar); 3.15 (s, 3H, CH$_3$O$_2$S—Ar); 2.65 (s, 3H, CH$_3$—Ar)

EXAMPLE 1

2,3-Ethylenedioxy-5-methylsulphonyl N-[3,β-(8-benzyl-8-azabicyclo[3.2.1]octyl)]benzamide (1)

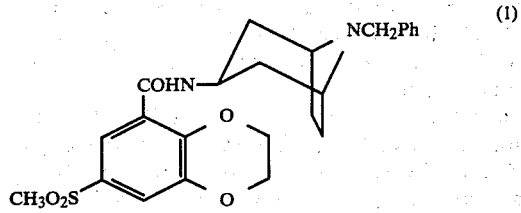

2,3-Ethylenedioxy-5-methylsulphonylbenzoic acid (1 g) was suspended in dry dichloromethane (30 ml) with oxalyl chloride (0.35 ml) and dry dimethylformamide (0.5 ml) added. The mixture was stirred at room temperature until it became homogeneous.

The solution was cooled to 0° C. and kept below this temperature during the dropwise addition of triethylamine (1.5 ml) in dry dichloromethane (15 ml), followed by the dropwise addition of 3β-amino-8-benzyl-8-azabicyclo[3.2.1]octane (0.86 g) in dry dichloromethane (15 ml).

The reaction mixture was allowed to warm to room temperature before being shaken with 10% sodium hydroxide soltuion (10 ml The organic layer was dried over anhydrous sodium sulphate, filtered and the solvent removed in vacuo to give a colourless oil (2 g) which was purified by column chromatography (silica, 3% methanol in ethyl acetate as eluant) and crystallised from ethanol-ether to give (1) (0.9 g, 50%), m.p. 211°-213° C., n.m.r. (CDCl$_3$): 1.77 (1H, d, aromatic H); 2.45 (1H, d, aromatic H); 2.5-3.0 (6H, m, aromatic H's and —CO-NUVS/H/ —); 5.3-5.9 (4H, m, —O—CH$_2$—CH$_2$—O—); 6.45 (2H, s, NCH$_2$Ph); 6.72 (2H, m, bridgehead H's); 7.0 (3H, s, —SO$_2$CH$_3$); 7.6-8.6 (8H, m, methylene H's).

EXAMPLE 2

2,4-Dimethoxy-5-methylsulphonyl-N[3β-(8-benzyl-8-azabicyclo{3.2.1}octyl)]benzamide (2)

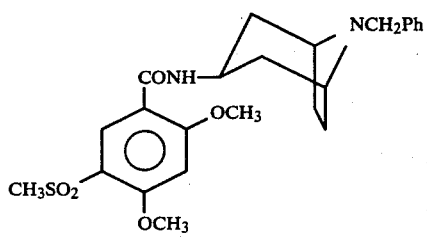

2,4-Dimethoxy-5-methylsulphonylbenzoic acid (0.52 g) was suspended in dry dichloromethane (20 ml) with oxalyl chloride (0.17 ml) and dry dimethylformamide (0.2 ml) was added. The mixture was stirred at room temperature until it became homogeneous.

The solution was cooled to 0° C. and kept below this temperature during the dropwise addition of triethylamine (0.75 ml) in dry dichloromethane (5 ml), followed by the dropwise addition of 3β-amino-8-benzyl-8-azabicyclo[3.2.1]octane (0.43 g) in dry dichloromethane (10 ml).

The reaction mixture was allowed to warm to room temperature before being shaken with 10% sodium hydroxide solution (10 ml). The organic layer was dried over anhydrous sodium sulphate, filtered and the solvent was removed in vacuo to give a colourless oil (0.9 g) which solidified on addition of a few drops of ether. Crystallisation from ethanol-ether gave the title compound (0.6 g, 68%).

nmr (CDCl$_3$) τ 1.4 (1H, s, aromatic H); 2.6-2.9 (6H, m, aromatic H's); 3.58 (1H, s, CONH); 6.04 (6H, s, 2 x —OCH$_3$); 6.5 (2H, s, —NCH$_2$Ph); 6.75 (2H, m, bridgehead H's); 6.92 (3H, s, —SO$_2$CH$_3$); 7.7-8.3 (8H, m, methylene H's)

EXAMPLE 3

2,3-Dimethoxy-5-methylsulphonyl-N[3β(8-benzyl-8-azabicyclo{3,2,1}octyl)]benzamide (3)

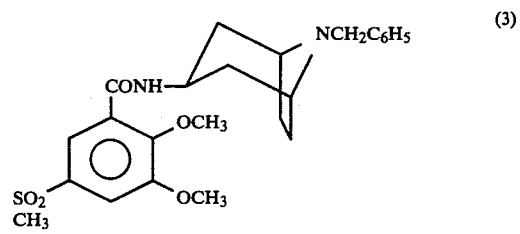

A solution of oxone* (0.3 g) in water (3 mls) was added dropwise to 2,3-dimethoxy-5-methylthio-N[3β(8-benzyl-8-azabicyclo{3,2,1}octyl)]benzamide (0.3 g) in methanol (10 mls) whilst keeping the temperature of the reaction mixture at 0° C.
*Potassium hydrogen persulphate The mixture was stirred at room temperature for 6 hours before the addition of a second portion of oxone (0,3 g) in water (3 mls). After stirring at room temperature for a further 12 hours, the resulting cloudy slurry was diluted with water and extracted with chloroform. The combined organic layers were washed with water and brine, dried over sodium sulphate and concentrated under reduced pressure to give a white solid (0.3 g). Purification by column chromatography (silica; 3% methanol/chloroform) gave the title compound (0.2 g, 69% yield). Observed mass 458.1874, C$_{24}$H$_{30}$N$_2$SO$_5$ requires 458.1875.

nmr. (CDCl$_3$) τ 1.8 (1H, d, aromatic H); 2.0 (1H, m, —CONH—); 2.15-2.8 (6H, m, aromatic H's); 5.55 (1H, m, 3αH); 5.95 (3H, s, OCH$_3$); 6.05 (5H, s, OCH$_3$ and NCH$_2$Ph); 6.35 (2H, m, bridgehead H's); 6.95 (3H, s, —SO$_2$CH$_3$); 7.2-8.2 (8H, m, methylene H's).

EXAMPLE 4

2-Methoxy-4-methyl-5-methylsulphonyl-N-[3-β-(8-benzyl-8-azabicyclo(3.2.1)octyl)]benzamide (4)

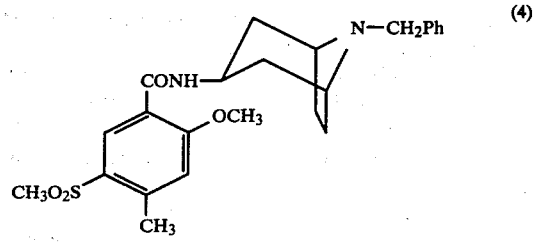

2-Methoxy-4-methyl-5-methylsulphonyl benzoic acid (2.0 g, 8.2 mmole) was dissolved in anhydrous dimethylformamide (20 ml) containing triethylamine (1.13 ml). The solution was cooled to 0° and ethyl chloroformate (0.89 g, 0.79 ml) was added dropwise. After a further 15 minutes, 8-benzyl-8-azabicyclo(3,2,1)octyl-3-β-amine (1.77 g, 82 mmole) in dry dimethylformamide was added in one portion. The mixture was allowed to reach ambiant temperatures overnight then evaporated in vacuo. The resulting solid was treated with water and aqueous potassium carbonate and extracted into ethyl acetate (3×100 ml). The combined organic extracts were dried (K$_2$CO$_3$) filtered and evaporated in vacuo (2.64 g). Recrystallization from ethyl acetate/ether gave the title compound (1.98 g; 55%) as colourless microcrystals mp 162° C.

nmr CDCl$_3$ δ 8.71 (s, 1H, 6—Ar—H); 7.6–6.7 (m+s, 7H, Ph—CH$_2$+3 Ar—H+NH); 4.3–4.0 (m, 1H,

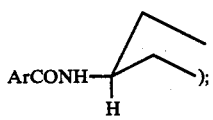

3.95 (s, 3H, OCH$_3$); 3.5 (s, 2H, PhCH$_2$—N); 3.4–3.2 (broad s, 2H, (>CH)$_2$); 3.0 (s, 3H, CH$_3$O$_2$S—Ar); 2.6 (s, (3H, CH$_3$—Ar); 2.4–1.3 (m, 8H, —(CH$_2$)$_4$—)

PHARMACOLOGICAL DATA

Increase in intragastric pressure

Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for 40 minute period after administration of compound. Student's "t" test was applied to the difference in average values obtained for spontaneous and post compound activity.

Anti-emetic activity in the dog

Compounds were administered subcutaneously 30 minutes prior to administration of a standard dose of apomorphine HCl (0.1 mg/kg subcutaneously) and the vomiting response compared to that obtained when the same animals were dosed with apomorphine HCl and vehicle only.

Dopamine Receptor Blocking Activity in the Central Nervous System

Compounds were tested for inhibition of apomorphine induced climbing in the mouse. The test is based on that described by Protais, P., Constantin, J. and Schwartz J. C. (1976), Psychopharmacology, 50, 1.6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—four paws only on walls; score 2—all paws on wall of cage. The scores at all 3 times and for each mouse are summed and mice drug treated orally compared to mice receiving apomorphine only. A saline only treated group is also included and any score, generally > 5% of maximum taken into account.

The results are as shown in Table 1

Toxicity

No toxic effects were observed in any of the above tests.

TABLE I

| Compound No. | I.G. Pressure mg/kg sc BASAL | I.G. Pressure mg/kg sc ADTN | Antiemetic mg/kg sc | CNS(climbing) mg/kg sc |
|---|---|---|---|---|
| 1 | 1.0 | 1.0 | I 0.1 | I 50 |
| 2 | I 1.0 | I 0.2 | .01 | ED$_{50}$ 1 |

I claim:

1. A compound of formula (I) and pharmaceutically acceptable salts thereof:

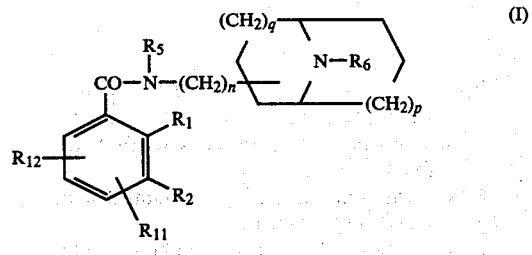

wherein:

n, p and q independently are 0 to 2;
R$_5$ is hydrogen or C$_{1-6}$ alkyl;
R$_6$ is C$_{1-7}$ alkyl or a group —(CH$_2$)$_s$R$_7$ where s is 0 to 2 and R$_7$ is a C$_{3-8}$ cycloalkyl group, or a group —(CH$_2$)$_t$R$_8$ where t is 1 or 2 and R$_8$ is C$_{2-5}$ alkenyl or a phenyl group optionally substituted by one or two substituents selected from C$_{1-6}$ alkyl, C$_{1-4}$ alkoxy, trifluoromethyl and halogen, or a thienyl group;
R$_{12}$ is C$_{1-6}$ alkylsulphonyl;
and either
R$_1$ is C$_{1-6}$ alkoxy or C$_{1-6}$ alkylthio; and one of R$_2$ and R$_{11}$ is hydrogen and the other is C$_{1-6}$ alkoxy, or hydroxy; or R$_1$ and R$_2$ together are C$_{1-3}$ alkylenedioxy; and R$_{11}$ is hydrogen, halogen, CF$_3$, C$_{1-6}$ alkoxy, hydroxy, nitro, C$_{1-7}$ acyl, amino, C$_{1-7}$ acylamino, aminocarbonyl optionally substituted by one or two C$_{1-6}$ alkyl, C$_{3-8}$ cycloalkyl, C$_{3-8}$ cycloalkyl C$_{1-4}$ alkyl, phenyl or phenyl C$_{1-4}$ alkyl groups any of which phenyl moieties may be substituted by one or more halogen, trifluoromethyl, C$_{1-6}$ alkoxy or nitro groups or N-disubstituted by C$_{4-6}$ polymethylene.

2. A compound according to claim 1 of formula (II):

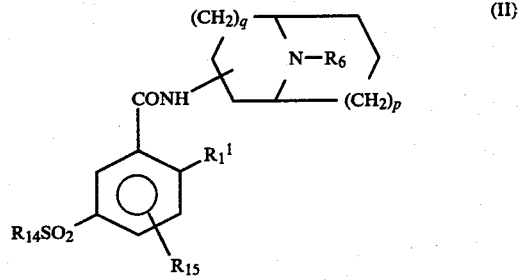

wherein:
R$_1^1$ is C$_{1-6}$ alkoxy;
R$_{14}$ is C$_{1-6}$ alkyl;
R$_{15}$ is C$_{1-6}$ alkoxy, or hydroxy;
and R$_6$, p and q are as defined in claim 1.

3. A compound according to claim 2 of formula (IV):

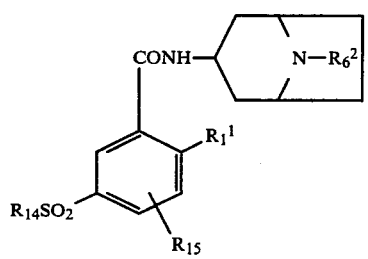

wherein:
$R_6^2$ is $C_{5-7}$ alkyl; a group $-(CH_2)_tR_8^1$ wherein t is 1 or 2 and $R_8^1$ is optionally substituted phenyl as defined in claim 1; cyclohexylmethyl, or 2-thienylmethyl.

4. A compound according to claim 2 wherein $R_1^1$ is methoxy and $R_{15}$ is methoxy.

5. A compound according to claim 2 wherein $R_{14}$ is methyl.

6. A compound according to claim 3 wherein $R_6^2$ is benzyl.

7. 2,3-Ethylenedioxy-5-methylsulphonyl N-[3,β-(8-benzyl-8-azabicyclo[3.2.1]octyl]benzamide or 2,4-Dimethoxy-5-methylsulphonyl-N[3]-(8-benzyl-8-azabicyclo[3.2.1]octyl)benzamide.

8. A compound according to claim 3, wherein $R_1^1$ is methoxy and $R_{15}$ is methoxy.

9. A compound according to claim 1, wherein $R_{12}$ is methylsulphonyl.

10. A compound according to claim 3, wherein $R_{14}$ is methyl.

11. A compound of the formula (XII):

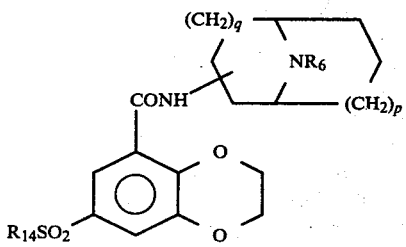

wherein
$R_6$ is $C_{1-7}$ alkyl or a group $-(CH_2)_sR_7$ where s is 0 to 2 and $R_7$ is a $C_{3-8}$ cycloalkyl group, or a group $-(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen, or a thienyl group;
$R_{14}$ is $C_{1-6}$ alkyl; and
p and q are independently 0, 1 or 2.

12. A compound of the formula (XIV)

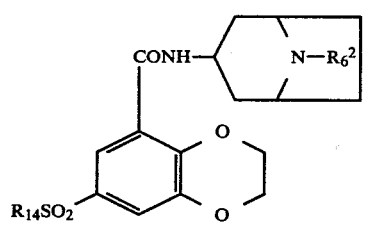

wherein $R_6^2$ is $C_{5-7}$ alkyl; $-(CH_2)_tR_8^1$, wherein t is 1 or 2 and $R_8^1$ is phenyl optionally substituted by one or two substituents selected from $C_{1-6}$ alkyl, $C_{1-4}$ alkoxy, trifluoromethyl and halogen; cyclohexylmethyl; or 2-thienylmethyl.

13. A compound according to claim 11, wherein $R_6$ is benzyl.

14. A compound according to claim 12, wherein $R_6^2$ is benzyl.

15. A compound according to claim 11, wherein $R_{14}$ is methyl.

16. A compound according to claim 12, wherein $R_{14}$ is methyl.

17. A pharmaceutical composition for the treatment of impaired gastric motility and/or for treatment of disorders of the central nervous system comprising an amount effective to improve gastric motility or an antipsychotic effective amount of a compound according to claim 1 or a pharmaceutically acceptable salt thereof and a pharmaceutically acceptable carrier.

18. A method of treating impaired gastric motility in mammals including humans comprising the administration to the sufferer of an effective amount of a compound according to claim 1 or a pharmaceutically acceptable salt thereof to the sufferer.

19. A method of treatment of disorders of the central nervous system in mammals including humans, comprising the administration to the sufferer of an effective amount of a compound according to claim 1 or a pharmaceutically acceptable salt thereof.

* * * * *